US012569265B2

(12) United States Patent
Baker et al.

(10) Patent No.: US 12,569,265 B2
(45) Date of Patent: Mar. 10, 2026

(54) DUAL MODE ACOUSTIC LITHOTRIPSY TRANSDUCER

(71) Applicant: GYRUS ACMI, INC., Westborough, MA (US)

(72) Inventors: Charles A. Baker, Rogers, MN (US); Arthur J. Bertelson, Buffalo, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 0 days.

(21) Appl. No.: 18/432,926

(22) Filed: Feb. 5, 2024

(65) Prior Publication Data

US 2024/0293136 A1 Sep. 5, 2024

Related U.S. Application Data

(60) Provisional application No. 63/487,900, filed on Mar. 2, 2023.

(51) Int. Cl.
*A61B 17/225* (2006.01)

(52) U.S. Cl.
CPC ...... *A61B 17/2258* (2013.01); *A61B 17/2255* (2013.01)

(58) Field of Classification Search
CPC ........................ A61B 17/2258; A61B 17/2255
See application file for complete search history.

(56) References Cited

U.S. PATENT DOCUMENTS 9,743,909 B1 * 8/2017 Sapozhnikov ....... A61B 5/0062
11,759,220 B2 * 9/2023 Baker ..................... H02N 2/06
606/127
2002/0010486 A1 * 1/2002 Hirt .................. A61B 17/22012
606/169
2006/0184076 A1 * 8/2006 Gill .................. A61B 17/22012
601/3
2008/0009885 A1 * 1/2008 Del Giglio ....... A61B 17/22012
606/128

(Continued)

OTHER PUBLICATIONS

Chen, Zitian, "A Novel Ultrasonic Bonding Transducer with Longitudinal and Lateral Operating Modes", Proceedings of the 7th International Conference on Nanomanufacturing (nanoMan2021), (2022), 248-257.

*Primary Examiner* — Baisakhi Roy

(74) *Attorney, Agent, or Firm* — Schwegman Lundberg & Woessner, P.A.

(57) ABSTRACT

An acoustic lithotripsy system can deliver acoustic energy to a target located within a patient. The system may include an acoustic transducer, the acoustic transducer including a first vibrator and a second vibrator. A system may include an impact member, coupled to the acoustic transducer, the impact member operable at a lower frequency than each of the first vibrator and the second vibrator. The system may further include controller circuitry, coupled to the acoustic transducer and the impact member, the controller circuitry including: an acoustic actuation control output, configured to selectively provide to at least one of the first vibrator or the second vibrator, an actuation control signal to control ablation of the target by the selected at least one of the first vibrator or the second vibrator. The first vibrator and/or or the second vibrator may be selected to operate with or without the impact member.

24 Claims, 5 Drawing Sheets

(56)         References Cited

U.S. PATENT DOCUMENTS

| | | | |
|---|---|---|---|
| 2009/0177085 A1* | 7/2009 | Maxwell | A61B 17/22004 |
| | | | 606/128 |
| 2011/0213279 A1* | 9/2011 | Britva | A61N 7/00 |
| | | | 601/2 |
| 2013/0303906 A1* | 11/2013 | Cain | A61N 7/00 |
| | | | 601/2 |
| 2018/0140835 A1* | 5/2018 | Sharma | G16H 10/60 |
| 2019/0053787 A1* | 2/2019 | Stigall | G06T 7/0012 |
| 2021/0018606 A1* | 1/2021 | McCaw | G01S 7/52079 |
| 2021/0038306 A1* | 2/2021 | McLoughlin | A61B 5/0084 |
| 2021/0309724 A1* | 10/2021 | Brown | A61K 9/10 |
| 2022/0022960 A1* | 1/2022 | Polejaev | A61B 5/0095 |
| 2022/0175269 A1* | 6/2022 | Lu | A61B 5/6851 |
| 2023/0346407 A1* | 11/2023 | Jiménez González | |
| | | | A61B 17/2258 |
| 2025/0010488 A1* | 1/2025 | Parthiban | A61B 34/37 |

* cited by examiner

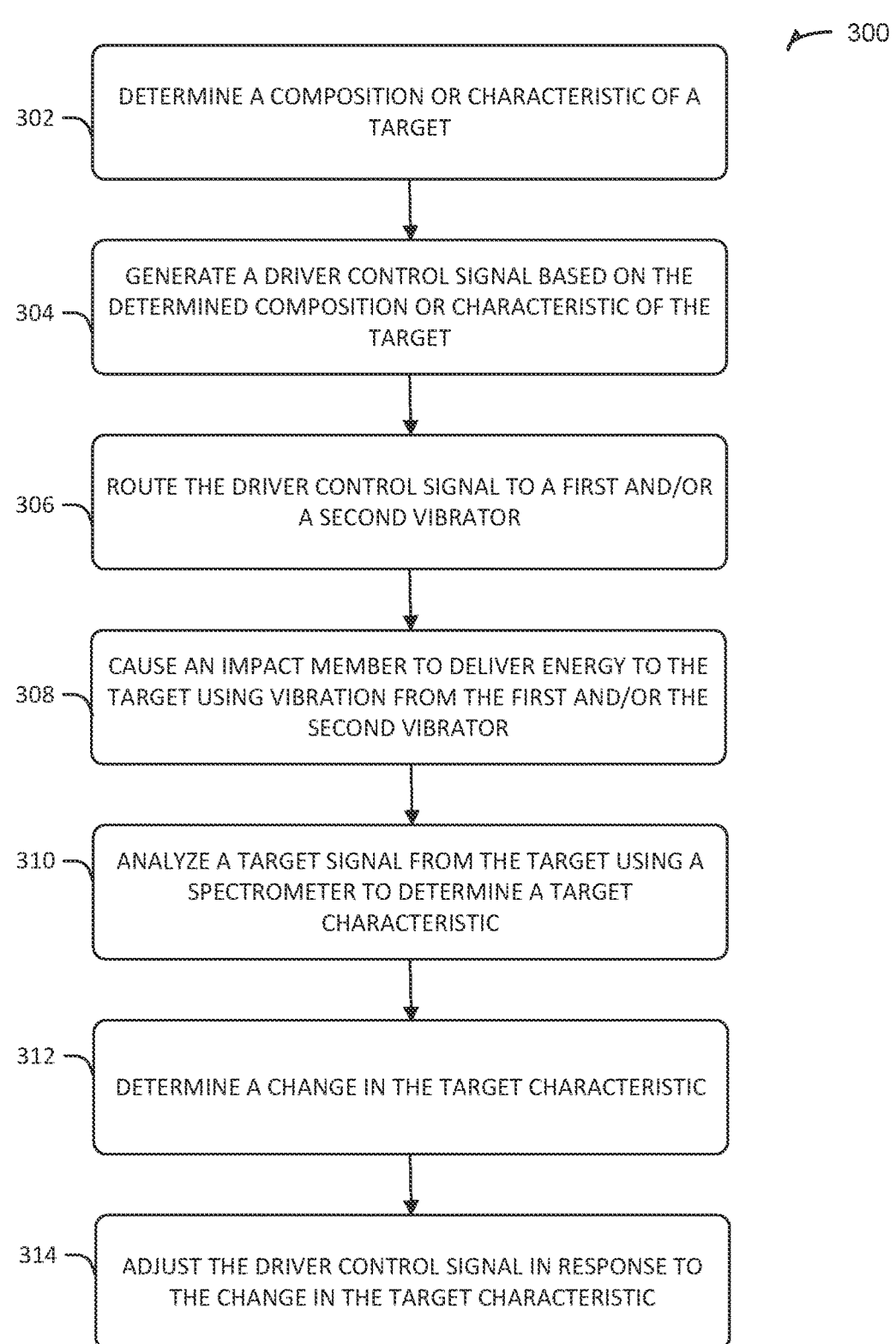

302 — DETERMINE A COMPOSITION OR CHARACTERISTIC OF A TARGET

304 — GENERATE A DRIVER CONTROL SIGNAL BASED ON THE DETERMINED COMPOSITION OR CHARACTERISTIC OF THE TARGET

306 — ROUTE THE DRIVER CONTROL SIGNAL TO A FIRST AND/OR A SECOND VIBRATOR

308 — CAUSE AN IMPACT MEMBER TO DELIVER ENERGY TO THE TARGET USING VIBRATION FROM THE FIRST AND/OR THE SECOND VIBRATOR

310 — ANALYZE A TARGET SIGNAL FROM THE TARGET USING A SPECTROMETER TO DETERMINE A TARGET CHARACTERISTIC

312 — DETERMINE A CHANGE IN THE TARGET CHARACTERISTIC

314 — ADJUST THE DRIVER CONTROL SIGNAL IN RESPONSE TO THE CHANGE IN THE TARGET CHARACTERISTIC

DUAL MODE ACOUSTIC LITHOTRIPSY TRANSDUCER

PRIORITY CLAIM

This application claims the benefit of priority to U.S. Provisional Patent Application Ser. No. 63/487,900, filed Mar. 2, 2023, the contents of which are incorporated herein by reference in their entirety.

TECHNICAL FIELD

The present disclosure relates to lithotripsy transducers, specifically to a lithotripsy using a transducer that includes multiple vibration devices respectively configured to vibrate at different frequencies and/or modes based on an observed or detected characteristic of a target.

BACKGROUND

Lithotripsy is a procedure used to break up targets, such as kidney stones, which are too large to (or cannot) pass naturally from the body. Lithotripsy can use lasers or acoustic waves to break up the stones. Acoustic shock wave lithotripsy can use acoustic shock waves emitted from a lithotripter, acoustic waveguide, or acoustic probe connected to a transducer to break up large stones, which can then be allowed to pass through the body (e.g., the urinary tract) or can be removed via a channel of a scope used to introduce the acoustic transducer.

Shock wave lithotripsy can be non-invasive or invasive. During invasive procedures, a probe or a scope, such as an endoscope, can be inserted into the body of a patient. The acoustic waves can cause an impact member located on the end of the scope to impact the stone and to cause the stone to break apart.

SUMMARY

Disclosed herein are systems and methods of use for acoustic lithotripsy. A system for delivering acoustic energy to a target (such as a kidney stone or a gall stone) located within a patient can comprise an acoustic transducer with a first vibrator and a second vibrator. The first and second vibrators can respectively include a piezoelectric material (or a piezoelectric stack) to cause the vibrator to move, oscillate, or the like, at a particular frequency and mode, such as in response to an applied electrical input signal. The first vibrator and the second vibrator can respectively vibrate at a frequency in an ultrasonic range and can vibrate at different frequencies in the ultrasonic range. For example, the first vibrator can vibrate at a frequency of 20 kilohertz (kHz) and the second vibrator can vibrate at a frequency of 100 kHz. Thus, the second vibrator can vibrate at a frequency greater than the first vibrator.

The system can also include an impact member such as a solenoid hammer or pneumatic actuator operable at a lower frequency than each of the first vibrator and the second vibrator. For example, the impact member can operate at a sub-ultrasonic frequency, such as 20 Hertz (Hz). In an example, the impact member can operate independently of the first vibrator and the second vibrator, can operate in conjunction with, or be driven by the first vibrator and/or the second vibrator.

The system can include controller circuitry coupled to the acoustic transducer and/or the impact member. The controller circuitry can include an acoustic actuation control output configured to selectively respectively provide the first vibrator and/or the second vibrator an actuation control signal to cause the first vibrator and/or the second vibrator to emit ultrasonic signals. For example, the actuation control signal can cause a first ultrasonic signal to be emitted from first vibrator and a second ultrasonic signal to be emitted from the second vibrator. The ultrasonic signals emitted from the first vibrator and/or the second vibrator can be used to control ablation of the target by the selected first vibrator and/or second vibrator. The first vibrator and/or the second vibrator can be selected to operate with or without the impact member and can be selected to operate individually or at the same time as each other. Stated another way, the first vibrator can be selected to operate on its own, the second vibrator can be selected to operate on its own, and the first and second vibrators can be selected to operate together, at the same time, thus allowing the transducer to operate in different modes.

The controller circuitry can include a target characteristic signal input configured to receive a target characteristic signal. The target characteristic signal can provide an indication of at least one of a target composition (e.g., a material or materials that the target is made up of) or another target characteristic, such as the size (e.g., length or width) or location (e.g., where in the anatomy of the patient the target is located). The composition or characteristic of the target can be determined using spectral or other analysis of the target by a spectrometer coupled to the controller circuitry. Details of laser control using a spectrometer can be found in U.S. patent application Ser. No. 16/947,485, the contents of which are incorporated in their entirety. The actuation control signal can be based at least in part on the received target characteristic signal. The actuation control signal can be adjusted, either by a physician user or by the controller circuitry in response to some change in a condition of the target. For example, the actuation control signal can be adjusted in response to a change in composition of the target (e.g., in a situation in which different layers of a stone is composed of a different material). Additionally, or alternatively, the actuation control signal can be adjusted based on a number of particles counted by a particle counter coupled to the controller circuitry as the target is reduced or ablated.

In an example, the first vibrator and the second vibrator can be at least partially separable. Or, stated differently, the transducer can be a single, solid piece in which the vibrators are electrically coupled to a generator or acoustic waveguide, or the transducer can be separated into two or more pieces, with one vibrator in one piece and the second vibrator in another piece. In an example in which the transducer is separated into two or more pieces, the first vibrator and the second vibrator can be connectable to each other such as by a tube and a mechanical connection. The mechanical connection can include at least one of a threaded connection, a pneumatic connection, or an over-center latch. The tube can maintain a seal between the first vibrator and the second vibrator and can be used to remove pieces of the target as the target is reduced or ablated.

Use of dual-action vibration such as in the system described herein can result in the ability to better and more efficiently fragment the target, leading to lower or reduced operating times and better patient outcomes with less surgical complications.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 3 is an example flowchart of a method for acoustic lithotripsy of a target located within a patient.

DETAILED DESCRIPTION

Acoustic or shock wave lithotripsy, uses ultrasound or other acoustic waves emitted from a lithotripter, acoustic waveguide, or acoustic probe connected to a transducer to break up one or more targets such as kidney stones (also referred to as "calculi") that are too large to pass naturally out of the body. The waves, such as ultrasonic or other acoustic waves, can be used to break up or fragment the target such as to permit the fragmented pieces to pass through and out of the body (e.g., the urinary tract) naturally, or can be removed via a scope and tube system within which an acoustic transducer is included or introduced.

Targets such as stones can have different compositions or be made of different materials. The composition of the stone generally determines a hardness level of the stone (e.g., how hard the stone is). The hardness level of the stone determines the acoustic frequency needed to fragment or break up the stone. For example, harder stones, such as stones formed from Calcium Oxalate, require more force and thus a lower-frequency wave to break up the stone. On the other hand, softer stones, such as stones formed from Uric Acid, require less force and thus a higher frequency to break up the stone. Often, stones can have a heterogenous or non-homogenous composition such that the stone is made up of different materials. For example, a kidney stone can have an outer portion or shell formed from Calcium Oxalate and have an inner portion formed from Uric Acid. Thus, the outer portion of the stone can be harder than the inner portion, or vice versa. Or, in another example, the entire stone can be a mix of hard and soft material. In such cases, waves of different frequencies can be used on different parts of the stone to more efficiently fragment the stone. For example, a lower-frequency wave can be used to break up a harder outer shell, and a higher frequency wave can be used to break up the softer inner portion.

Ultrasonic or other acoustic lithotripsy can benefit from dual-action or other multi-action vibration. This can include using separate vibration stacks or members (or vibrators) in the acoustic transducer that can operate at different frequencies. This can lead to greater fragmentation ability which, in turn, can result in lower operating times and better patient outcomes. The inventors have identified a need for the acoustic waves emitted by the transducer to be established or adjusted during a procedure based, for example, on how the stone is breaking down or apart (e.g., an amount of fragmentation), by composition of the stone or changing composition of the stone, or the like.

Figure 1:
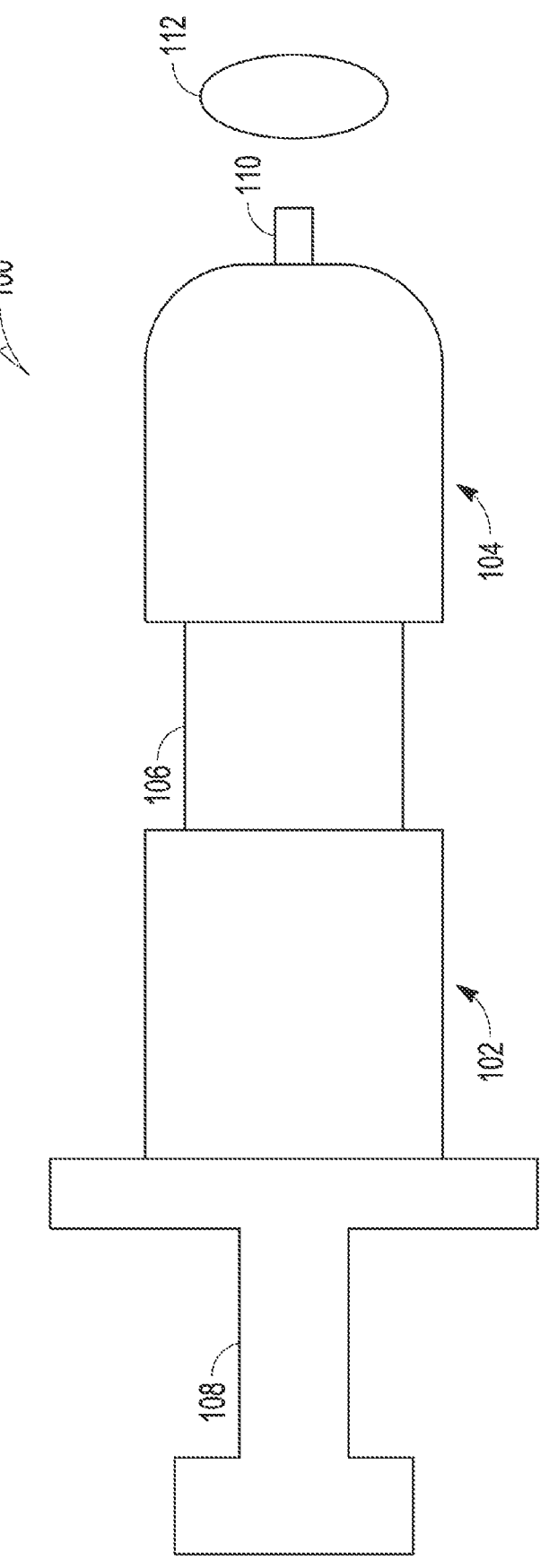
FIG. 1 illustrates an example of an acoustic lithotripsy transducer with a dual vibration stack configuration.

FIG. 1 illustrates an example of an acoustic lithotripsy transducer 100 with a dual vibration stack configuration. In FIG. 1, the transducer can include a first vibration portion (a vibrating stack or a vibrating member; hereinafter a first vibrator 102) and a second vibration portion, stack or member (hereinafter a second vibrator 104). For example, the first vibrator 102 and/or the second vibrator 104 can be located in an interior portion of the acoustic lithotripsy transducer 100, such as within a housing forming the body of the acoustic lithotripsy transducer 100. In an example, the acoustic lithotripsy transducer 100 can include an impact member assembly 108 (e.g., an assembly such that it can include a solenoid, a projectile, a pneumatic actuator, a spring, or a free mass impacted by the projectile) located at a proximal end of the acoustic lithotripsy transducer 100. For example, the impact member assembly 108 can be included in or form a portion of a handle of the acoustic lithotripsy transducer 100. The acoustic lithotripsy transducer 100 can also include an acoustic waveguide or an acoustic probe or any suitable elements, such as a solenoid, a spring, a pneumatic actuator, a free mass, a ring, a sleeve, etc. located at or attached to a distal end of the acoustic lithotripsy transducer 100. In an example in which the impact member assembly 108 is located at the proximal end of the acoustic lithotripsy transducer 100, a mass and projectile type impact member can be caused to travel through the impact member assembly 108 to generate acoustic energy that is transmitted to an acoustic probe 110 which can be added to energy provided by an ultrasonic signal from the first vibrator 102 and/or the second vibrator 104 to make contact with a target 112. In another example embodiment (e.g., in which the impact member is a solenoid), the impact member assembly 108 can be located at the distal end of the acoustic lithotripsy transducer 100, proximate to the acoustic probe 110. In an example, an acoustic signal, such as an ultrasonic signal can be emitted by the first vibrator 102 and/or the second vibrator 104 (which themselves are driven by an electrical signal) and be sent to the impact member assembly 108 and/or acoustic probe 110. The acoustic lithotripsy transducer 100 can optionally include a middle portion or middle block 106 that separates the first vibrator 102 from the second vibrator 104. The second vibrator 104 can be located at or toward a proximal end of the acoustic lithotripsy transducer 100 and the first vibrator 102 can be located at or toward a distal end of the acoustic lithotripsy transducer 100.

In an example, the first vibrator 102 can be configurable to operate at a first frequency, such as at a first ultrasonic frequency such as 20 kHz, and the second vibrator 104 can be configurable to operate at a substantially different or higher frequency such as 100 kHz. Thus, the second vibrator 104 can be configured to vibrate at a higher or greater frequency than the first vibrator 102.

The first vibrator 102 and/or the second vibrator 104 can transmit energy such as via an acoustic or ultrasonic signal to the impact member assembly 108 to cause an impact member to contact or transmit energy to a target, such as a stone to be fragmented. Alternatively, the impact member assembly 108 can be driven by a separate actuator different from the first and/or second vibrators. Therefore, the acoustic lithotripsy transducer 100 can optionally include an elongated member that is at least partially insertable into the body of a patient such that an impact member can impact the target and cause the target to break apart or fragment. The impact member assembly 108 can include a solenoid hammer or solenoid driver. The impact member assembly 108 can include at least one of a spring or a free mass. In an example, the impact member assembly 108 can include a cylindrically shaped rod or tube, such as can be formed from a metal such as surgical steel or aluminum.

The impact member can be any suitable or desired shape and made from any suitable or desired material such that it is capable of being driven by the first vibrator 102 and/or the second vibrator 104 and/or a separate, different actuator to fragment a target. In such an example, a frequency of the impact member may be sub-ultrasonic (e.g., twenty Hertz or less) and may be an effect of the ultrasonic vibration of the first vibrator 102 and/or the second vibrator 104. Stated differently, vibrations from the first vibrator 102 and/or second vibrator 104 can cause the motion of the impact member at a sub-ultrasonic frequency.

In another example, the impact member can be operable the sub-ultrasonic acoustic frequency but can be driven by a signal independently of either of the first vibrator 102 and/or the second vibrator 104. For example, the impact member can be driven by a signal from a separate actuator different from the first vibrator 102 and/or the second vibrator 104.

The first vibrator 102 and/or the second vibrator 104 can include a piezoelectric material or a stack of piezoelectric material (or any similar material) and can be capable of generating different types of modes of vibration, or waves. For example, the first vibrator 102 can be configured to emit a longitudinal wave and the second vibrator 104 can be configured to emit a transverse wave. Alternatively, the first vibrator 102 can be configured to emit a transverse wave and the second vibrator 104 can be configured to emit a longitudinal wave. In another example, each of the first vibrator 102 and the second vibrator 104 can be able to selectively emit either a longitudinal wave or a transverse wave, such as can be based on a user selection or a determination by controller circuitry based on factors such as the location of the target, one or more characteristics (e.g., composition, composition profile, size, shape, etc.) of the target.

The first vibrator 102 and the second vibrator 104 can be electrically controlled by any source of electrical energy and can be capable of running independently of each other or simultaneously. Or, stated differently, the first vibrator 102 can be operable on its own, the second vibrator 104 can be operable on its own, or the first vibrator 102 and second vibrator 104 can be operable at the same time. The ability to use the vibrators independently of each other and transmit different wave types through the vibrators allows a physician the flexibility to alter modes (e.g., longitudinal and transverse modes) of operation of the acoustic lithotripsy transducer 100, which can be useful in a variety of lithotripsy scenarios. For example, when a determination is made that less retropulsion (pushing the target away from the acoustic lithotripsy transducer 100) is desirable (such as because of a location of a kidney stone within the kidney or the composition or hardness level of the kidney stone), a single vibrator running at a high frequency and/or emitting a transverse wave can be desired. Other times, such as when a kidney stone is very hard, it can be desirable to emit energy from the first vibrator 102 and the second vibrator 104 at the same time such that the frequency from the first vibrator 102 and the frequency from the second vibrator 104 can be superimposed to allow the stone to be fragmented easier, more quickly, etc.

Figure 2:
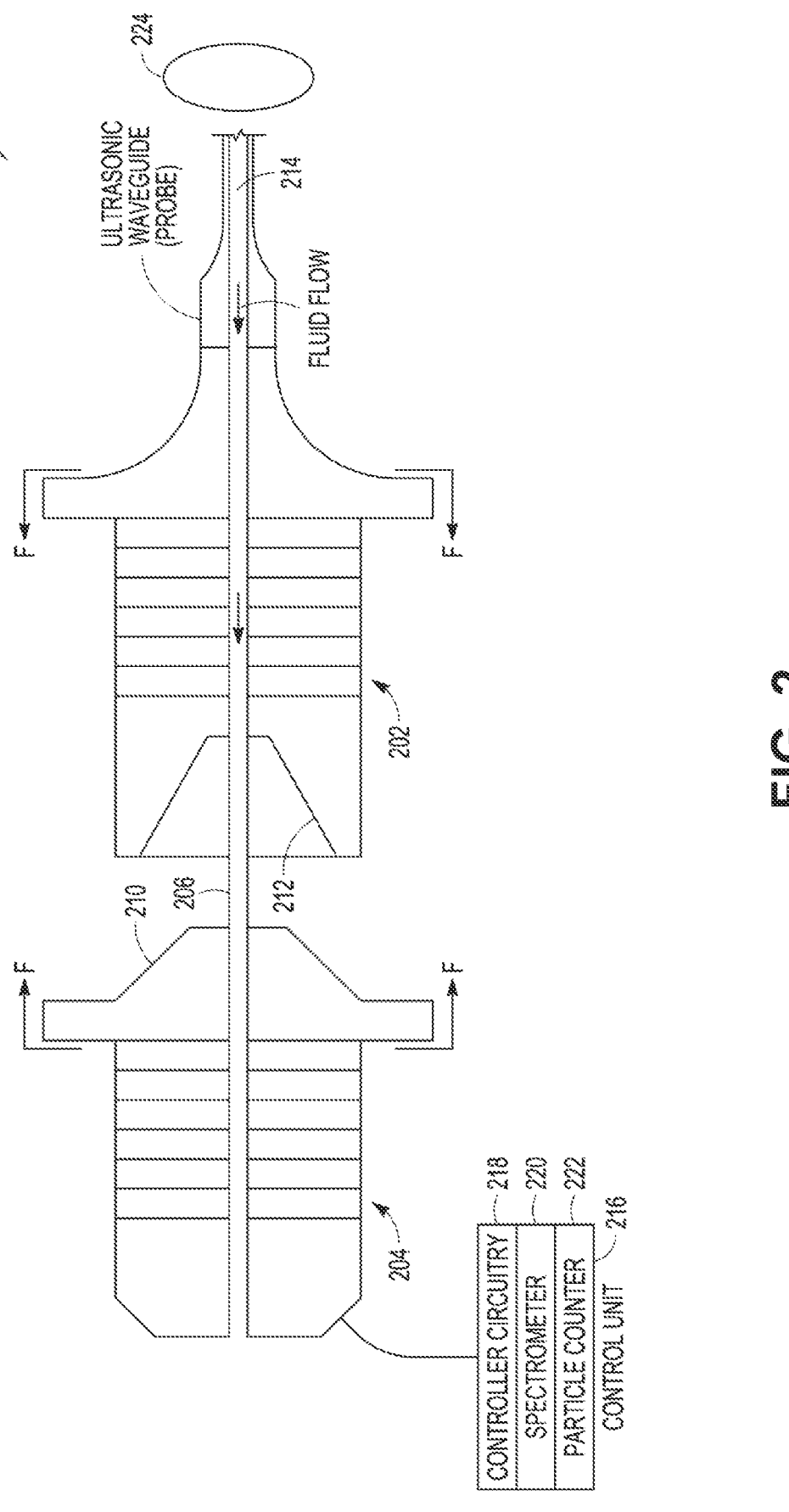
FIG. 2 illustrates an example of a separable dual vibration stack configuration of an acoustic transducer.

FIG. 2 illustrates an example of a separable dual vibration stack configuration of an acoustic transducer. FIG. 2 illustrates a cross-sectional view of an acoustic transducer 200 in which a first vibrator 202 is at least partially separable from a second vibrator 204. In such an example, the first vibrator 202 and the second vibrator 204 can be configured to be able to be separated such as in a middle portion, similar to middle block 106 in the acoustic lithotripsy transducer 100 discussed above. The first vibrator 202 can contain a first separation portion 210 and the second vibrator 204 can contain a second separation portion 212 (collectively "separation portions"). The separation portions can be shaped so that the first separation portion 210 and the second separation portion 212 fit together to form a coupling. For example, one of the separation portions can include an extended or bumped out portion and the other of the separation portions can include a cavity such that the separation portions can be brought together by a force (as denoted by the directional arrows) in a way such that the extended portion fits into the cavity.

In an example, the force to bring the separation portions together can be a mechanical force. The mechanical force can be implemented via a mechanical connection. The mechanical connection can include two or more threaded members that can be screwed, twisted, or otherwise brought together, a pneumatic connection (such as one or more pneumatic actuators), an over-center latch or lever, or some combination thereof, capable of mating the separation portions together and capable of maintaining energy transmission to the first vibrator 202 and/or the second vibrator 204. An acoustic waveguide 214 (e.g., an ultrasonic waveguide or probe) can be connected to the acoustic transducer 200. One or more electrical signals can drive the first vibrator 202 and/or the second vibrator 204 to vibrate at a frequency, such as an ultrasonic frequency in a vibration mode (e.g., longitudinal or transverse mode). The ultrasonic signals from the first vibrator 202 and/or the second vibrator 204 can be transmitted to the acoustic waveguide 214 to transmit energy to a target 224. In the example of the acoustic transducer 200 illustrated in FIG. 2, the first vibrator 202 can be constantly in an active or "on" state, or stated differently, the first vibrator 202 can be always "on". The second vibrator 204 can be activated when the second vibrator 204 is connected to the first vibrator 202 when the separation points are brought together via the mechanical connection. Thus, in some examples, the second vibrator 204 can be activated or "on" only when it is connected to the first vibrator 202 via the mechanical connection. This can allow a dual action lithotripsy in which an actuation control signal sent to the first vibrator 202 and an actuation control signal sent to the second vibrator 204 can be superimposed. As discussed above for FIG. 1, the second vibrator 204 can be configured to vibrate at a different (e.g., a higher) frequency than the first vibrator 202. Thus, the actuation control signal sent to the first vibrator 202 can be a lower frequency than the actuation control signal sent to the second vibrator 204.

In an example, either of the acoustic lithotripsy transducer 100 or the acoustic transducer 200 can include a tube, such as tube 206, connecting the vibrators. Tube 206 (e.g., a floating lumen tube) can connect the first vibrator 202 and the second vibrator 204, even when the first vibrator 202 and the second vibrator 204 are separated from each other. In such an example, the tube 206 can maintain a seal between the first vibrator 202 and the second vibrator 204 so that fluid (e.g., water, saline, or the like) can flow through the tube 206 (as denoted by the arrows) during a procedure. Furthermore, the tube 206 can allow fragmented pieces of a target such as a kidney stone to be passed through, such as when the acoustic transducer 200 is connected to a vacuum pump or source so as to suck fragmented pieces of the target through the tube 206 and out of the body of the patient. The tube 206 can be fixed with respect to the first vibrator 202 and movable (e.g., slidable) with respect to the second vibrator

204. For example, the tube 206 can retract into the second vibrator 204 when the first vibrator 202 and the second vibrator 204 are connected to each other via the mechanical connection, in which state the tube 206 maintains a seal between the first vibrator 202 and the second vibrator 204.

In an example, either of the acoustic lithotripsy transducer 100 or the acoustic transducer 200 can be included as a part of a system that includes a control unit, such as control unit 216. The control unit 216 can include or be part of a computer or other similar machine, such as the machine described in FIG. 4 below, and can contain controller circuitry 218, a spectrometer 220, and/or a particle counter 222. The control unit 216 can include more or less components such as those described and/or illustrated in FIG. 4 as desired. The controller circuitry 218 can include a target characteristic signal input configured to receive a target characteristic signal providing an indication related to the target. The indication can include a composition of the target, such as a material composition, a size of the target, or any other similar target characteristic. The controller circuitry 218 can be configured to emit the actuation control signal based at least in part on the received target characteristic signal.

The controller circuitry 218 can be coupled to a spectrometer 220 which can be included as a part of the control unit 216 or can be coupled or connected to the control unit 216 such as to be able to perform spectral analysis on the target characteristic signal to determine a target characteristic, such as a composition of the target. The controller circuitry 218 can further include an acoustic actuation control output configured to selectively provide the first vibrator 202 or the second vibrator 204 an actuation control or driver control signal. In an example, the actuation control signal can be an any electrical signal capable of driving the vibrators and causing the vibrators to emit an acoustic or ultrasonic signal, which can in turn be focused and transmitted to an impact member. The actuation control signal sent to the first vibrator 202 can be different than the actuation control signal sent to the second vibrator 204, such as can be based on one or more factors such as the frequency at which the first vibrator 202 and the second vibrator 204 are configured to vibrate. The actuation control signal can also control the type of wave (e.g., longitudinal or transverse) sent to the vibrators. The control unit 216 can also include or be coupled to a particle counter 222. The particle counter 222 can be configured to count the number of particles generated by the target as the target is fragmented. The particle counter 222 can be located in the control unit 216 or it can include a portion that can be physically located at some other portion of the acoustic transducer 200 such as in a handle or handpiece, where it can count the number of particles being removed from the patient's body through the tube 206.

The control unit 216 and/or the controller circuitry 218 can be coupled to an Artificial Intelligence (AI) or Machine Learning (ML) system that can allow the controller circuitry 218 to adjust the actuation control signal based on the number of particles counted by the particle counter, the target characteristic, and/or the target composition. Additionally, or alternatively, the actuation control signal can be adjusted by a determined change in the target composition, target characteristic, or the number of particles counted by the particle counter. For example, the system can determine that a kidney stone is formed from calcium oxalate and can adjust the actuation control signal to cause a lower frequency wave to be emitted from the first vibrator 202. The system can then determine that the composition of the stone has changed to uric acid and adjust the actuation control signal to cause a higher frequency wave to be emitted from the second vibrator 204. Similarly, the system can determine that the target is not fragmenting or breaking apart at the same rate (e.g., because the number of particles being counted by the particle counter 222 is slowed) and adjust the actuation control signal accordingly.

FIG. 3 is an example of a flowchart of a method 300 for acoustic lithotripsy of a target located within a patient. The method 300 can include a series of operations or steps that can be utilized to perform the method 300. At 302, a composition or characteristic of a target can be determined. The composition can be a material composition determined by spectral analysis or by visual inspection by a physician. For example, this can include determining whether the target, such as a kidney stone is made from uric acid or calcium oxalate. The composition of the target can assist in determining other characteristics of the target such as a hardness level, thickness, or the like. At 304, a driver control signal can be generated based on the determined composition or characteristic of the target, and at 306 the driver control signal can be routed to at least one of a first vibrator or a second vibrator included in an acoustic lithotripsy transducer. At 308, an impact member coupled to the first and/or second vibrator can deliver energy to the target using vibration from the first and/or second vibrator. At 310, a target signal from the target (e.g., light reflected from the target) can be analyzed using a spectrometer to determine a target characteristic. For example, the spectrometer can determine the composition of the target, which can, in turn, determine a hardness level for the target. At 312 a change in the target characteristic can be determined. At 314, the driver control signal can be adjusted in response to the change in the target characteristic. The change in the target characteristic, such as a change in the composition of the target can be determined by the analysis by the spectrometer or a change in the number of particles being fragmented from the target determined by a particle counter. For example, if the hardness of the target increases, then the driver control signal can be increased. Alternatively, if the hardness of the target decreases, the driver control signal can be lowered or reduced. Similarly, if the position of the target changes during ablation, such as being pushed away from the impact member, the type of wave being emitted can be adjusted (e.g., from a longitudinal wave to a transverse wave).

In an example, the spectral analysis on the target can be performed continuously, recurrently, at a predetermined interval, periodically, etc. Hence, the spectral analysis can be updated throughout a medical procedure such as a stone ablation to monitor the stone or target to determine whether a change has occurred with respect to the target. In response to a change, the driver control signal can be adjusted accordingly. The adjustment can be made by a user of the transducer such as by depressing a foot switch or a foot pedal, or engaging some actuation member, for example pushing a button or flipping a switch on the transducer or a handpiece connected to the transducer, through a touch-screen graphical user interface (GUI) or through any similar mode of activation. Additionally, or alternatively, the adjustment can be made by a controller, without requiring user intervention, such as the controller circuitry 218 discussed above for FIG. 2. In such an example, the controller circuitry can cause the adjustment to the driver control signal automatically or can suggest to the user that a change be made and allow the user to accept or reject the change.

Figure 4:
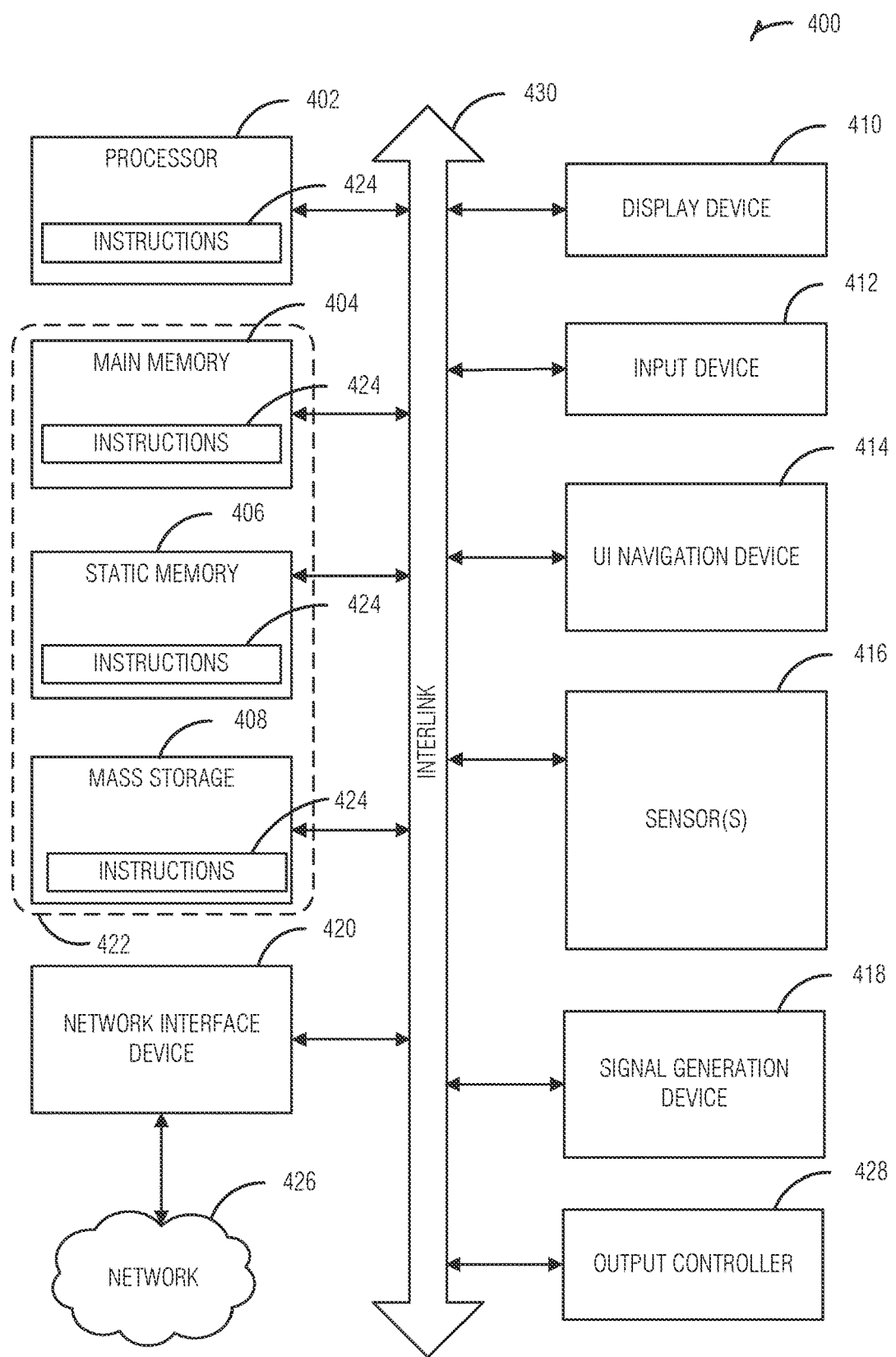
FIG. 4 is a block diagram illustrating an example of a machine upon which one or more embodiments may be implemented.

FIG. 4 a block diagram illustrating an example of a machine upon which one or more embodiments can be implemented. In some embodiments, the machine 400 can operate as a standalone device or can be connected (e.g., networked) to other machines. For example, the machine 400 can be included in, coupled to, or connected to the control unit 216, the controller circuitry 218, the particle counter 222 and/or the spectrometer 220 to cause any or all of those components (or any other components of included in or coupled to the control unit 216 perform one or more of their operations described above). In a networked deployment, the machine 400 can operate in the capacity of a server machine, a client machine, or both in server-client network environments. In an example, the machine 400 can act as a peer machine in peer-to-peer (P2P) (or other distributed) network environment. The machine 400 can be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, can include, or can operate by, logic or a number of components, or mechanisms. Circuit sets are a collection of circuits implemented in tangible entities that include hardware (e.g., simple circuits, gates, logic, etc.). Circuit set membership can be flexible over time and underlying hardware variability. Circuit sets include members that can, alone or in combination, perform specified operations when operating. In an example, hardware of the circuit set can be immutably designed to carry out a specific operation (e.g., hardwired). In an example, the hardware of the circuit set can include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components can be used in more than one member of more than one circuit set. For example, under operation, execution units can be used in a first circuit of a first circuit set at one point in time and reused by a second circuit in the first circuit set, or by a third circuit in a second circuit set at a different time.

Machine 400 (e.g., a computer system) can include a hardware processor 402 (e.g., a central processing unit (CPU), a graphics processing unit (GPU), a hardware processor core, field programmable gate array (FPGA), or any combination thereof), a main memory 404 and a static memory 406, some or all of which can communicate with each other via an interlink (e.g., bus) 430. The machine 400 can further include a display unit 410, an alphanumeric input device 412 (e.g., a keyboard), and a user interface (UI)

navigation device 414 (e.g., a mouse). In an example, the display unit 410, input device 412 and UI navigation device 414 can be a touch screen display. The machine 400 can additionally include a storage device 408 (e.g., a drive unit), a signal generation device 418 (e.g., a speaker), a network interface device 420, and one or more sensors 416, such as a global positioning system (GPS) sensor, compass, accelerometer, or other sensor. The machine 400 can include an output controller 428, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 408 can include a machine readable medium 422 on which is stored one or more sets of data structures or instructions 424 (e.g., software) embodying or used by any one or more of the techniques or functions described herein. The instructions 424 can also reside, completely or at least partially, within the main memory 404, within static memory 406, or within the hardware processor 402 during execution thereof by the machine 400. In an example, one or any combination of the hardware processor 402, the main memory 404, the static memory 406, or the storage device 408 can constitute machine readable media.

While the machine readable medium 422 is illustrated as a single medium, the term "machine readable medium" can include a single medium or multiple media (e.g., a centralized or distributed database, and/or associated caches and servers) configured to store the one or more instructions 424.

The term "machine readable medium" can include any medium that is capable of storing, encoding, or carrying instructions for execution by the machine 400 and that cause the machine 400 to perform any one or more of the techniques of the present disclosure, or that is capable of storing, encoding, or carrying data structures used by or associated with such instructions. Non-limiting machine readable medium examples can include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media can include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 424 can further be transmitted or received over a communications network 426 using a transmission medium via the network interface device 420 utilizing any one of a number of transfer protocols (e.g., frame relay, internet protocol (IP), transmission control protocol (TCP), user datagram protocol (UDP), hypertext transfer protocol (HTTP), etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards), IEEE 802.15.4 family of standards, peer-to-peer (P2P) networks, among others. In an example, the network interface device 420 can include one or more physical jacks (e.g., Ethernet, coaxial, or phone jacks) or one or more antennas to connect to the communications network 426. In an example, the network interface device 420 can include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding, or carrying instructions for execution by the machine 400, and includes digital or analog communications signals or other intangible medium to facilitate communication of such software.

Figure 5:
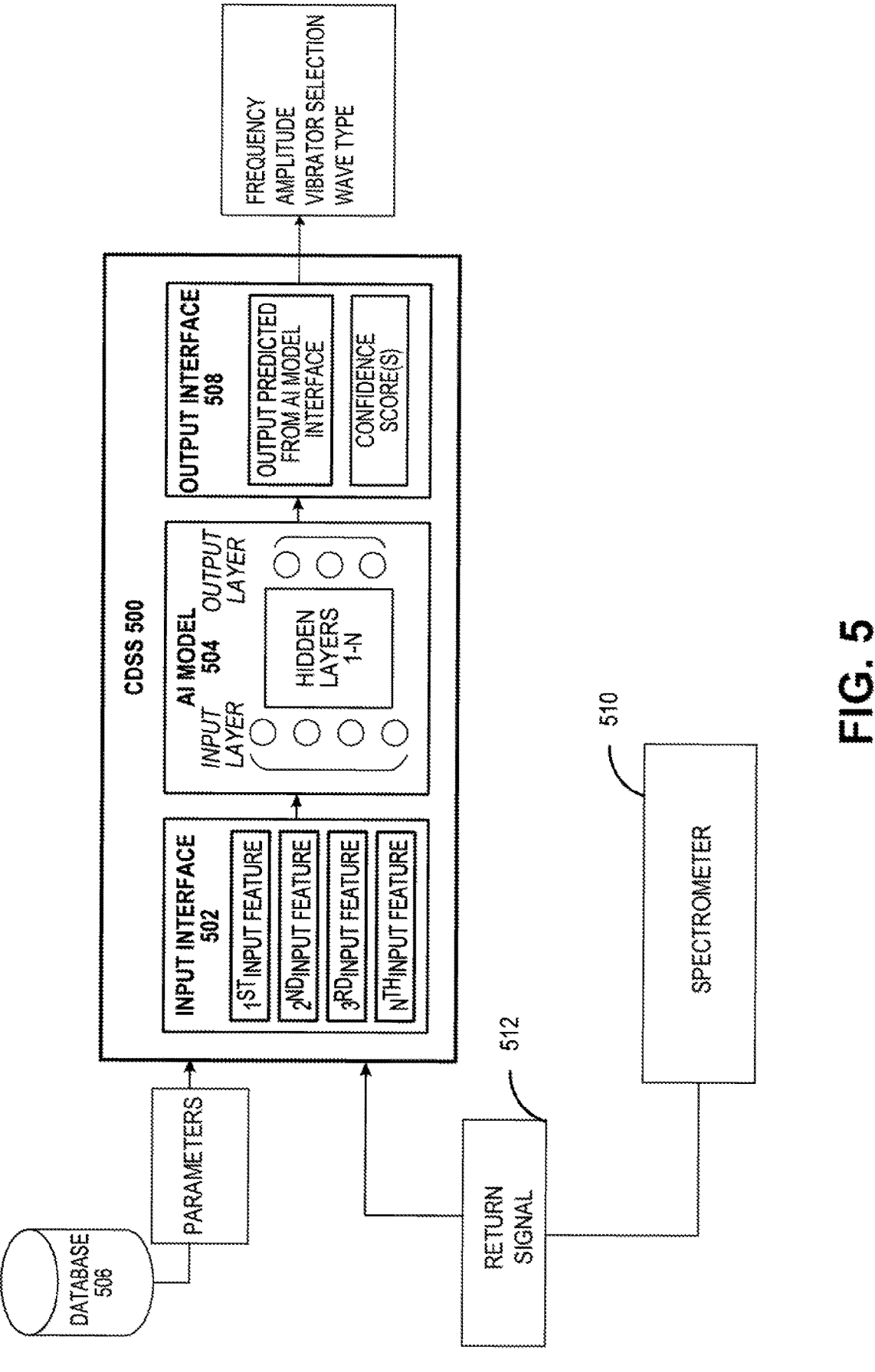
FIG. 5 illustrates an example of a schematic diagram of an exemplary computer-based clinical decision support system (CDSS).

FIG. 5 illustrates a schematic diagram of an exemplary computer-based clinical decision support system (CDSS) 500 that is configured to determine information or characteristics about a target, such as size, composition, hardness, density, or any similar characteristic or information about the target based on spectroscopic analysis of a signal from the target. The CDSS 500 can include an input interface 502 through which parameters such as the type of transducer, the components connected to the transducer, location of the target in the patient's body, or the like, which are specific to a patient's procedure are provided as input features to an artificial intelligence (AI) model 504, a processor which performs an inference operation in which the parameters are applied to the AI model to generate the determination of the target characteristics and optimal settings for the transducer (e.g., whether to use the first vibrator, the second vibrator, or both at vibrators at the same time) to reduce or ablate the target, a frequency or amplitude of the ablation control signal, the type of wave to be emitted (e.g., longitudinal or transverse), etc., and an output interface 508 through which the determined target characteristics and settings can be communicated to a user, e.g., a clinician.

The input interface 502 can include a direct data link between the CDSS 500 and one or more medical devices that generate at least some of the input features. For example, the input interface 502 can transmit information from the spectrometer 220, information from the particle counter 222, and/or or information about a signal returned from the target directly to the CDSS 500 during a therapeutic and/or diagnostic medical procedure. In an example, about the transducer, the vibration sources, or the like, to be used during the procedure can be stored in a database 506. Additionally, or alternatively, the input interface 502 can be a classical user interface that facilitates interaction between a user and the CDSS 500. For example, the input interface 502 can facilitate a user interface through which the user can manually enter the information about transducer, the vibration sources, the scope, the optical components, signals to block or allow, etc. Additionally, or alternatively, the input interface 502 can provide the CDSS 500 with access to an electronic patient record or the components being used during the procedure from which one or more input features can be extracted. In any of these cases, the input interface 502 can be configured to collect one or more of the following input features in association with one or more of a specific patient, a type of medical procedure, a type of scope, a type of transducer, features of the transducers or the components thereof, or the like, on or before a time at which the CDSS 500 is used to assess the input features will take place.

An example of an input feature can include a type of the transducer used during the medical procedure.

An example of an input feature can include a location of the target in the patient's body.

An example of an input feature can include a type of component connected to the transducer.

An example of an input feature can include signal information of a return signal 512 received at the spectrometer 510 from the target.

An example of an input feature can include the spectral analysis of the target received from the spectrometer 510.

Based on one or more of the above input features, the processor performs an inference operation using the AI model 504 to generate determined characteristics of the target such as the size of the target, the composition of the target, hardness, density, or any similar characteristic. For example, input interface 502 can deliver the one or more of the input features listed above into an input layer of the AI model 504 which propagates these input features through the AI model 504 to an output layer. The AI model 504 can provide a computer system the ability to perform tasks, without explicitly being programmed, by making inferences based on patterns found in the analysis of data. The AI model 504 explores the study and construction of algorithms (e.g., machine-learning algorithms) that can learn from existing data and make predictions about new data. Such algorithms operate by building an AI model from example training data in order to make data-driven predictions or decisions expressed as outputs or assessments.

Examples of two modes for machine learning (ML) can include: supervised ML and unsupervised ML. Supervised ML uses prior knowledge (e.g., examples that correlate inputs to outputs or outcomes) to learn the relationships between the inputs and the outputs. The goal of supervised ML is to learn a function that, given some training data, best approximates the relationship between the training inputs and outputs so that the ML model can implement the same relationships when given inputs to generate the corresponding outputs. Unsupervised ML is the training of an ML algorithm using information that is neither classified nor labeled and allowing the algorithm to act on that information without guidance. Unsupervised ML is useful in exploratory analysis because it can automatically identify structure in data.

Tasks for supervised ML can include classification problems and regression problems. Classification problems, also referred to as categorization problems, aim at classifying items into one of several category values (for example, is this object an apple or an orange?). Regression algorithms aim at quantifying some items (for example, by providing a score to the value of some input). Some examples of supervised-ML algorithms are Logistic Regression (LR), Naive-Bayes, Random Forest (RF), neural networks (NN), deep neural networks (DNN), matrix factorization, and Support Vector Machines (SVM).

Some possible tasks for unsupervised ML include clustering, representation learning, and density estimation. Some examples of unsupervised-ML algorithms are K-means clustering, principal component analysis, and autoencoders.

Another type of ML is federated learning (also known as collaborative learning) that trains an algorithm across multiple decentralized devices holding local data, without exchanging the data. This approach stands in contrast to traditional centralized machine-learning techniques where all the local datasets are uploaded to one server, as well as to more classical decentralized approaches which often assume that local data samples are identically distributed. Federated learning enables multiple actors to build a common, robust machine learning model without sharing data, thus allowing to address critical issues such as data privacy, data security, data access rights and access to heterogeneous data.

In some examples, the AI model 504 can be trained continuously or periodically prior to performance of the inference operation by the processor. Then, during the inference operation, the patient specific input features provided to the AI model 504 can be propagated from an input layer, through one or more hidden layers, and ultimately to an output layer that corresponds to the information about the target. For example, when evaluating the spectroscopic analysis of the signal from the target, the system can determine one or more characteristics of the target. During and/or subsequent to the inference operation, the information about the target can be communicated to the user via the output interface 508 (e.g., a user interface (UI)) and/or automatically cause the transducer connected to the processor to perform a desired action. For example, based on the composition of the target the system can cause the transducer to activate one or both of the vibrators, select or adjust a frequency and/or amplitude of the vibration signal, select or adjust a wave type to be emitted, etc. The actions can be performed automatically based on the analysis by the AI model or can be presented to the user as recommended settings that the user can accept, decline, or adjust as desired.

ADDITIONAL NOTES AND EXAMPLES

Example 1 is a system for acoustic lithotripsy for delivering acoustic energy to a target located within a patient, the system comprising: an acoustic transducer, the acoustic transducer including a first vibrator and a second vibrator; and controller circuitry, coupled to the acoustic transducer, the controller circuitry including: an acoustic actuation control output, configured to selectively provide to at least one of the first vibrator or the second vibrator, an actuation control signal to control ablation of the target by the selected at least one of the first vibrator or the second vibrator.

In Example 2, the subject matter of Example 1 optionally includes an impact member, coupled to the acoustic transducer, the impact member operable at a lower frequency than each of the first vibrator and the second vibrator, and wherein the controller circuitry includes: a target characteristic signal input, configured to receive a target characteristic signal providing an indication of at least one of a target composition or other target characteristic, wherein the actuation control signal is based at least in part on the received target characteristic signal, and wherein the selected at least one of the first vibrator or the second vibrator is selected to operate one of with or without the impact member.

In Example 3, the subject matter of any one or more of Examples 1-2 optionally include wherein the actuation control signal is an electronic signal that causes the first vibrator to emit a first ultrasonic signal and the second vibrator to emit a second ultrasonic signal, and wherein the second vibrator is configured to vibrate at a greater frequency than the first vibrator.

In Example 4, the subject matter of any one or more of Examples 1-3 optionally include a distal portion of an elongated member at least partially insertable into a body of a patient; and at least one of an acoustic waveguide or acoustic probe.

In Example 5, the subject matter of any one or more of Examples 1~4 optionally include wherein the first vibrator and the second vibrator includes a piezoelectric material, and wherein one of the first vibrator or the second vibrator is configured to emit a longitudinal wave, and wherein the other of the first vibrator or the second vibrator is configured to emit a transverse wave.

In Example 6, the subject matter of any one or more of Examples 2-5 optionally include wherein the impact member includes a solenoid hammer.

In Example 7, the subject matter of any one or more of Examples 2-6 optionally include wherein the impact member includes at least one of a spring or a free mass.

In Example 8, the subject matter of any one or more of Examples 1-7 optionally include a spectrometer, coupled to the controller circuitry, the spectrometer configured to analyze a composition or characteristic of the target.

In Example 9, the subject matter of Example 8 optionally includes wherein the controller circuitry is configured to adjust the control signal in response to a change in composition of the target based on information from the spectrometer.

In Example 10, the subject matter of any one or more of Examples 1-9 optionally include a particle counter coupled to the controller circuitry configured to count a number of particles as the target is reduced or ablated.

In Example 11, the subject matter of Example 10 optionally includes wherein the controller circuitry is configured to adjust the control signal based on a number of particles counted by the particle counter.

In Example 12, the subject matter of any one or more of Examples 1-11 optionally include wherein the first vibrator and the second vibrator are at least partially separable and are connectable to each other by a tube and a mechanical connection.

In Example 13, the subject matter of Example 12 optionally includes wherein the mechanical connection includes at least one of a threaded connection, a pneumatic connection, or an over-center latch.

In Example 14, the subject matter of any one or more of Examples 12-13 optionally include wherein the controller circuitry includes an operational mode in which the first vibrator is constantly in an activated state and wherein the second vibrator is activated when connected to the first vibrator via the mechanical connection.

In Example 15, the subject matter of any one or more of Examples 12-14 optionally include wherein the tube is fixed with respect to the first vibrator and movable with respect to the second vibrator, and wherein the tube retracts into the second vibrator when the first vibrator and the second vibrator are connected to each other via the mechanical connection, in which state the tube maintains a seal between the first vibrator and the second vibrator.

Example 16 is a method for acoustic lithotripsy of a target located within a patient, the method comprising: determining a target composition or other target characteristic of the target; generating a driver control signal based on the determined target characteristic of the target; routing the driver control signal to at least one of a first vibrator or a second vibrator; and causing an impact member coupled to at least one of the first vibrator or the second vibrator to deliver energy to the target using vibration from at least one of the first vibrator or the second vibrator.

In Example 17, the subject matter of Example 16 optionally includes analyzing a target signal from the target using a spectrometer for determining the target composition or other target characteristic; and adjusting the driver control signal in response to a change in target composition of the target.

In Example 18, the subject matter of any one or more of Examples 16-17 optionally include counting a number of particles generated by the target using a particle counter; and adjusting the driver control signal based on the number of particles counted by the particle counter.

Example 19 is an acoustic transducer comprising: a first vibrator; a second vibrator at least partially separable from the first vibrator; an impact member coupled to at least one of the first vibrator or the second vibrator; an acoustic waveguide coupled to at least one of the impact member or the first vibrator or the second vibrator; a tube partially connecting the first vibrator to the second vibrator and maintaining a seal therebetween; and a connecting member configured to engage the first vibrator to the second vibrator.

In Example 20, the subject matter of Example 19 optionally includes configured to include an operating state in which the first vibrator is constantly activated, and the second vibrator is selectively activated when connected to the first vibrator via the connecting member.

In Example 21, the subject matter of any one or more of Examples 19-20 optionally include wherein the tube is fixed with respect to the first vibrator and slidable with respect to the second vibrator, and wherein the tube retracts into the second vibrator when the first vibrator and the second vibrator are connected to each other via the connecting member, and wherein the tube maintains a seal between the first vibrator and the second vibrator.

The above detailed description includes references to the accompanying drawings, which form a part of the detailed description. The drawings show, by way of illustration, specific embodiments that can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is to allow the reader to quickly ascertain the nature of the technical disclosure and is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the embodiments should be determined with reference to the appended claims, along with the full scope of equivalents to which such claims are entitled.

What is claimed is:

1. A system for acoustic lithotripsy for delivering acoustic energy to a lithotripsy target located internally within a patient, the system comprising:

an acoustic transducer, the acoustic transducer including a first vibrator and a second vibrator respectively operating at different corresponding first and second vibration frequencies, and respectively providing corresponding wave types that are distinct from each other; and controller circuitry, coupled to the acoustic transducer, the controller circuitry including:

an acoustic actuation control output, configured to:

receive, from one or more optical sensors, a target characteristic input signal indicating a lithotripsy target composition; and selectively provide to at least one of the first vibrator or the second vibrator, an actuation control signal to control ablation of the lithotripsy target by the selected at least one of the first vibrator or the second vibrator so that the at least one of the first vibrator or the second vibrator selectively emits its respective wave type and frequency based on the lithotripsy target composition determined using the target characteristic input signal, wherein the first vibrator emits its respective wave type toward the lithotripsy target when the lithotripsy target composition meets a first lithotripsy target composition characteristic and the second vibrator emits its respective wave type toward the lithotripsy target when the lithotripsy target composition meets a second lithotripsy target composition characteristic.

2. The system of claim 1, comprising:

an impact member, coupled to the acoustic transducer, the impact member operable at a lower frequency than each of the first vibrator and the second vibrator, and wherein the controller circuitry includes:

a target characteristic signal input, configured to receive the target characteristic input signal, wherein the actuation control signal is based at least in part on the received target characteristic input signal, wherein the first lithotripsy target composition characteristic corresponds to the lithotripsy target composition being above a hardness threshold amount and the second lithotripsy target composition characteristic corresponds to the lithotripsy target composition being below the hardness threshold amount, and wherein the selected at least one of the first vibrator or the second vibrator is selected to operate one of with or without the impact member.

3. The system of claim 2, wherein the impact member includes a solenoid hammer.

4. The system of claim 2, wherein the impact member includes at least one of a spring or a free mass.

5. The system of claim 1, wherein the actuation control signal is an electronic signal that causes the first vibrator to emit a first ultrasonic signal and the second vibrator to emit a second ultrasonic signal.

6. The system of claim 1, further comprising:
a distal portion of an elongated member insertable into a body of a patient; and
at least one of an acoustic waveguide or acoustic probe.

7. The system of claim 1, wherein the first vibrator and the second vibrator includes a piezoelectric material, and wherein one of the first vibrator or the second vibrator is configured to emit a longitudinal wave, and wherein the other of the first vibrator or the second vibrator is configured to emit a transverse wave.

8. The system of claim 1, comprising:
a spectrometer, coupled to the controller circuitry, the spectrometer configured to analyze the target characteristic input signal.

9. The system of claim 8, wherein the controller circuitry is configured to adjust the actuation control signal in response to a change in composition of the lithotripsy target based on information from the spectrometer.

10. The system of claim 1, further comprising:
a particle counter coupled to the controller circuitry configured to count a number of particles as the lithotripsy target is reduced or ablated.

11. The system of claim 10, wherein the controller circuitry is configured to adjust the actuation control signal based on a number of particles counted by the particle counter.

12. The system of claim 1, wherein the first vibrator and the second vibrator are separable and are connectable to each other by a tube and a mechanical connection.

13. The system of claim 12, wherein the mechanical connection includes at least one of a threaded connection, a pneumatic connection, or an over-center latch.

14. The system of claim 12, wherein the controller circuitry includes an operational mode in which the first vibrator is constantly in an activated state and wherein the second vibrator is activated when connected to the first vibrator via the mechanical connection.

15. The system of claim 12, wherein the tube is fixed with respect to the first vibrator and movable with respect to the second vibrator, and wherein the tube retracts into the second vibrator when the first vibrator and the second vibrator are connected to each other via the mechanical connection, in which state the tube maintains a seal between the first vibrator and the second vibrator.

16. A method for acoustic lithotripsy of a lithotripsy target located internally within a patient, the method comprising:
determining a lithotripsy target composition by receiving, from one or more optical sensors, a target characteristic input signal indicating the lithotripsy target composition;
generating a driver control signal based on the determined lithotripsy target composition;
routing the driver control signal to at least one of a first vibrator or a second vibrator; and
causing an impact member coupled to at least one of the first vibrator or the second vibrator to deliver energy to the lithotripsy target using vibration from at least one of the first vibrator or the second vibrator, wherein the first and second vibrators respectively vibrate at different corresponding first and second vibration frequencies and with corresponding wave types that are distinct from each other so that the at least one of the first vibrator or the second vibrator selectively emits its respective wave type and frequency based on the lithotripsy target composition determined using the target characteristic input signal, wherein the first vibrator emits its respective wave type toward the lithotripsy target when the lithotripsy target composition meets a first lithotripsy target composition characteristic and the second vibrator emits its respective wave type when the lithotripsy target composition meets a second lithotripsy target composition characteristic.

17. The method of claim 16, comprising:
analyzing a target signal from the lithotripsy target using a spectrometer for determining the lithotripsy target composition; and
adjusting the driver control signal in response to a change in the lithotripsy target composition of the lithotripsy target.

18. The method of claim 16, comprising:
counting a number of particles generated by the lithotripsy target using a particle counter; and
adjusting the driver control signal based on the number of particles counted by the particle counter.

19. The method of claim 16, wherein the first vibrator is configured to provide a first wave type being a transverse wave type, and wherein the second vibrator is configured to provide a second wave type that is a longitudinal wave, and wherein the method comprises adjusting emission of the respective wave types in response to a change in the lithotripsy target composition.

20. An acoustic transducer comprising:
a first vibrator, configured to vibrate at a first vibration frequency and a first wave type;
a second vibrator separable from the first vibrator, the second vibrator configured to vibrate at a second vibration frequency that is different from the first vibration frequency and with a second wave type that is distinct from the first wave type, wherein the first vibrator and the second vibrator are configured to be selectively coupled to a lithotripsy target based on a lithotripsy target composition determined from a target characteristic input signal received from one or more optical sensors;
an impact member coupled to at least one of the first vibrator or the second vibrator;
an acoustic waveguide coupled to at least one of the impact member or the first vibrator or the second vibrator;
a tube partially connecting the first vibrator to the second vibrator and maintaining a seal therebetween; and
a connecting member configured to engage the first vibrator to the second vibrator, wherein the first vibrator emits its respective wave type to the lithotripsy target when the lithotripsy target composition meets a first lithotripsy target composition characteristic and the second vibrator emits its respective wave type when the lithotripsy target composition meets a second lithotripsy target composition characteristic.

21. The acoustic transducer of claim 20, configured to include an operating state in which the first vibrator is constantly activated, and the second vibrator is selectively activated when connected to the first vibrator via the connecting member.

22. The acoustic transducer of claim 20, wherein the tube is fixed with respect to the first vibrator and slidable with respect to the second vibrator, and wherein the tube retracts into the second vibrator when the first vibrator and the second vibrator are connected to each other via the connecting member, and wherein the tube maintains a seal between the first vibrator and the second vibrator.

23. The system of claim 1, wherein the first vibrator is configured to provide a first wave type being a transverse wave type, and wherein the second vibrator is configured to provide a second wave type that is a longitudinal wave, and wherein the controller circuitry is configured to adjust emission of the respective wave types in response to a change in the lithotripsy target composition.

24. The acoustic transducer of claim 20, the first vibrator is configured to provide a first wave type being a transverse wave type, and wherein the second vibrator is configured to provide a second wave type that is a longitudinal wave, and wherein the first and second vibrators are configured to be adjusted to adjust emission of the respective wave types in response to a change in the lithotripsy target composition.

*   *   *   *   *